(12) United States Patent
Minezaki et al.

(10) Patent No.: US 6,685,673 B2
(45) Date of Patent: Feb. 3, 2004

(54) CONTINUOUS LIQUID INFUSION DEVICE

(75) Inventors: Susumu Minezaki, Tokyo (JP); Hiroshi Takahashi, Tokyo (JP)

(73) Assignee: Orchis Company Limited, Tokyo (JP)

( * ) Notice: Subject to any disclaimer, the term of this patent is extended or adjusted under 35 U.S.C. 154(b) by 0 days.

(21) Appl. No.: 10/188,068

(22) Filed: Jul. 3, 2002

(65) Prior Publication Data
US 2002/0165490 A1 Nov. 7, 2002

Related U.S. Application Data

(63) Continuation of application No. PCT/JP01/00890, filed on Feb. 8, 2001.

(30) Foreign Application Priority Data

May 26, 2000 (JP) ........................................ 2000-157163

(51) Int. Cl.[7] ............................................... A61M 37/00
(52) U.S. Cl. ........................ 604/143; 604/146; 222/336
(58) Field of Search ................................. 604/151, 143, 604/146; 222/336

(56) References Cited

U.S. PATENT DOCUMENTS

| | | | | |
|---|---|---|---|---|
| 3,349,767 A | * | 10/1967 | Gidlund | 604/143 |
| 4,180,067 A | * | 12/1979 | Derlien | 604/131 |
| 5,024,664 A | | 6/1991 | Mitchell | |
| 5,807,337 A | * | 9/1998 | Yamada et al. | 604/143 |
| 6,139,530 A | * | 10/2000 | Hiejima et al. | 604/140 |
| 6,200,054 B1 | * | 3/2001 | Chen | 401/150 |

FOREIGN PATENT DOCUMENTS

| | | |
|---|---|---|
| EP | 0 715 861 A1 | 6/1996 |
| JP | 8-257119 | 10/1996 |
| JP | 11-276581 | 10/1999 |
| JP | 2000-014776 | 1/2000 |
| JP | 3068265 | 2/2000 |
| WO | WO 92/01484 | 2/1992 |

* cited by examiner

Primary Examiner—Brian L. Casler
Assistant Examiner—Jeremy Thissell
(74) Attorney, Agent, or Firm—Staas & Halsey LLP

(57) ABSTRACT

The invention relates to a continuous liquid infusion device which can be easily prepared for operation with small force, and can infuse liquid at constant infusion rate and amount over a long time. It comprises a liquid syringe section and a driving pump section mounted on the liquid syringe section, wherein sliding the pressing arm of the driving pump section upward leads to axially slides the piston in the negative pressure chamber to produce a negative pressure therein; and using returning force of the piston under the negative pressure, the liquid pushout plunger barrel is biased toward the upper edge of a pressing member through a locking member engaged with the piston so as to push out liquid in the liquid syringe from the liquid infusion port. Further, only the liquid syringe is disposable while the vacuum pump barrel on the driving side is good for repeated use (reusable).

4 Claims, 18 Drawing Sheets

CONTINUOUS LIQUID INFUSION DEVICE

CROSS REFERENCE TO RELATED APPLICATION

This application is a continuation application of International Application PCT/JP01/00890, filed Feb. 8, 2001, and designating the U.S.

BACKGROUND OF THE INVENTION

1. Field of the Invention

The present invention relates to a continuous liquid infusion device, and particularly to a continuous liquid infusion device which is simply preparable for operation with small force, easy to handle, and capable of infusing liquid at a predetermined infusion rate and amount over a long period of time.

2. Description of the Related Art

In infusing liquid for treatment into human or animal bodies, liquid is continuously infused at a predetermined flow rate for a long time in some cases. For example, there are cases which require transfusion of a nutrition supplement solution or the like, or liquid infusion such as an anticoagulant compound, an anticancer compound, a demulcent, a local anesthesia compound, a blood sugar value adjusting compound, or the like in a solution state into a body of a patient from his/her vein, artery, hypodermis, epidural space, or the like at a predetermined flow rate over a long time.

In such cases, an infusion device using an electric syringe pump, an infusion device (balloon infuser) which performs infusion through the use of contraction force of a balloon having elasticity, an infusion device utilizing elasticity of a spring, and so on are conventionally used.

However, the infusion device using the electric syringe pump described above has a large weight and is inconvenient for the patient to carry when he/she moves as well as it is complicatedly structured and expensive. Further, since the balloon infuser does not have constant contraction force of the balloon and liquid discharging force, it is difficult to continuously infuse liquid at a constant flow rate so liquid sometimes remains in the balloon. Furthermore, with these conventional infusion devices driven by the balloon or the spring, it is difficult to maintain precision of the predetermined infusion rate and amount of liquid over a long time.

Accordingly, proposed is a liquid infusion device in which a second cylinder internally maintained under negative pressure by operation of a piston or the like is mounted on a first cylinder filled with liquid, and the liquid in the first cylinder is pushed out by the piston which is driven by negative pressure in the second cylinder (Japanese Utility Model Laid-open No. Hei 5-20751, Japanese Patent Laid-open No. Hei 5-176997, and International Publication No. WO95/28977).

However, these conventional infusion devices utilizing negative pressure are not easy to handle because they need large force for operating the piston or the like to form negative pressure. For example, the piston is slidably inserted and fitted into a center barrel which is inserted in the center of the second cylinder, and hence sliding resistance due to an air-tight holding member such as an O-ring, which is arranged between the center barrel and the piston for inserting and fitting the piston into the center barrel airtightly, is large or leakage or the like of air is prevented in forming negative pressure in the second cylinder at the same time of infusing liquid, which requires large force when the piston is pushed up.

Moreover, since the infusion devices have the particular structure such as the center barrel provided in the second cylinder, they need to be handled with caution and their manufacturing cost is high.

Furthermore, it is difficult to maintain negative pressure, which is driving force for infusion, constant over a long time and there is a problem in precision of an infusion rate and amount of liquid.

An object of the present invention is to provide a continuous liquid infusion device capable of infusing liquid into a liquid syringe with smaller force compared with that required for the conventional liquid infusion device utilizing negative pressure, preparable for operation with small force by a small driving pump section, and facilitating intra-arterial infusion requiring pressure of 300 mmHg or more. Further, it is another object of the present invention to provide a continuous liquid infusion device which is simply structured and easy to handle, in which a liquid syringe section and a driving pump section are separable, and which is advantageous in terms of cost, whose leakage of air and sliding resistance are not too large, and which is capable of performing infusion at a constant infusion rate and liquid amount and is excellent in durability.

SUMMARY OF THE INVENTION

In order to solve the aforementioned problem, the present invention provides a continuous liquid infusion device comprising a liquid syringe section and a driving pump section mounted on the liquid syringe section. The liquid syringe section has a liquid infusion port at one end, an opening at the other end connected with a bottom end part of the driving pump section, a liquid filling chamber in communication with the liquid infusion port, and a pushing member including a peripheral edge in sliding contact with an inner circumferential wall of the liquid filling chamber and being slidable due to the peripheral edge to reciprocate air-tightly and liquid-tightly in an axis direction of the liquid syringe section. The driving pump section has a liquid pushout plunger barrel including the bottom end part abutting on an upper edge of the pushing member and at least two pressing arms connected to the bottom end part and inserted and fitted into the liquid filling chamber along the inner circumferential wall, and an internal negative pressure cylinder to be inserted and fitted into the liquid pushout plunger barrel, including a negative pressure chamber therein, and having a piston inserted and fitted thereinto, for producing negative pressure by sliding in the axis direction in the negative pressure chamber air-tightly. In the continuous liquid infusion device, sliding the pressing arms of the driving pump section toward an upper end causes the piston to slide and be pushed up in the negative pressure chamber in the axis direction to produce negative pressure in the negative pressure chamber, and the liquid pushout plunger barrel is biased toward the upper edge of the pushing member via a locking member engaged with the piston by utilizing returning force of the piston due to the negative pressure so that the biased pushing member pushes liquid in the liquid syringe out of the liquid infusion port.

According to another aspect of the present invention, provided is the continuous liquid infusion device characterized in that the liquid syringe section and the driving pump section are structured to be separable.

Further, according to still another aspect of the present invention, provided is the continuous liquid infusion device characterized in that the liquid syringe section is structured of a plurality of auxiliary syringe parts and has pressing arms and bottom end parts corresponding to the respective pushing members, the pressing members being to be inserted and fitted into the plurality of auxiliary syringe parts.

Furthermore, according to yet another aspect of the present invention, provided is a continuous liquid infusion device which comprises: a first structure having a vacuum pump barrel which includes an open/close valve at its front end and an open rear end, a piston fitted into the vacuum pump barrel air-tightly, a stopper capable of locking the piston at the rear end of the vacuum pump barrel against atmospheric pressure, and a pusher movable in the same direction as that of the piston outside the vacuum pump barrel; and a second structure having a liquid syringe which includes a liquid port at its front end and an open rear end, and a piston fitted into the liquid syringe liquid-tightly, wherein the first structure and the second structure are removably connected.

Moreover, according to yet another aspect of the present invention, provided is the continuous liquid infusion device characterized in that the first structure and the second structure are connectable in a state in which the front end of the vacuum pump barrel of the first structure extends further forward than the front end of the liquid syringe.

Further, according to yet another aspect of the present invention, provided is the continuous liquid infusion device characterized in that the first structure has dual pushers and the second structure has dual liquid syringes.

As described above, the continuous liquid infusion device according to the present invention is structured to bias the liquid pushout plunger barrel via the locking member engaged with the piston and push out liquid in the liquid syringe by utilizing returning force of the piston due to negative pressure inside the vacuum pump barrel, which enables liquid infusion at constant infusion rate and amount over a long period of time and easy handling, and brings about an advantage in terms of cost.

BRIEF DESCRIPTION OF THE DRAWINGS

The nature, principle, and utility of the invention will become more apparent from the following detailed description when read in conjunction with the accompanying drawings in which like parts are designated by identical reference numbers, in which:

FIGS. 20(A) to 20(C) are explanatory views of an operation state of the infusion device in FIG. 15, in which FIG. 20(A) shows a standby state, FIG. 20(B) shows an intermediate process of infusion, and FIG. 20(C) shows the completion of infusion.

DESCRIPTION OF THE PREFERRED DEMBODIMENTS

A continuous liquid infusion device according to the present invention (hereinafter referred to as "infusion device of the present invention") will be explained based on the attached drawings.

FIG. 1 to FIG. 6 show an example of a separation type infusion device as an embodiment of the infusion device of the present invention. An infusion device 1 of the present invention has a liquid syringe section 2 and a driving pump section 3.

Figure 1:
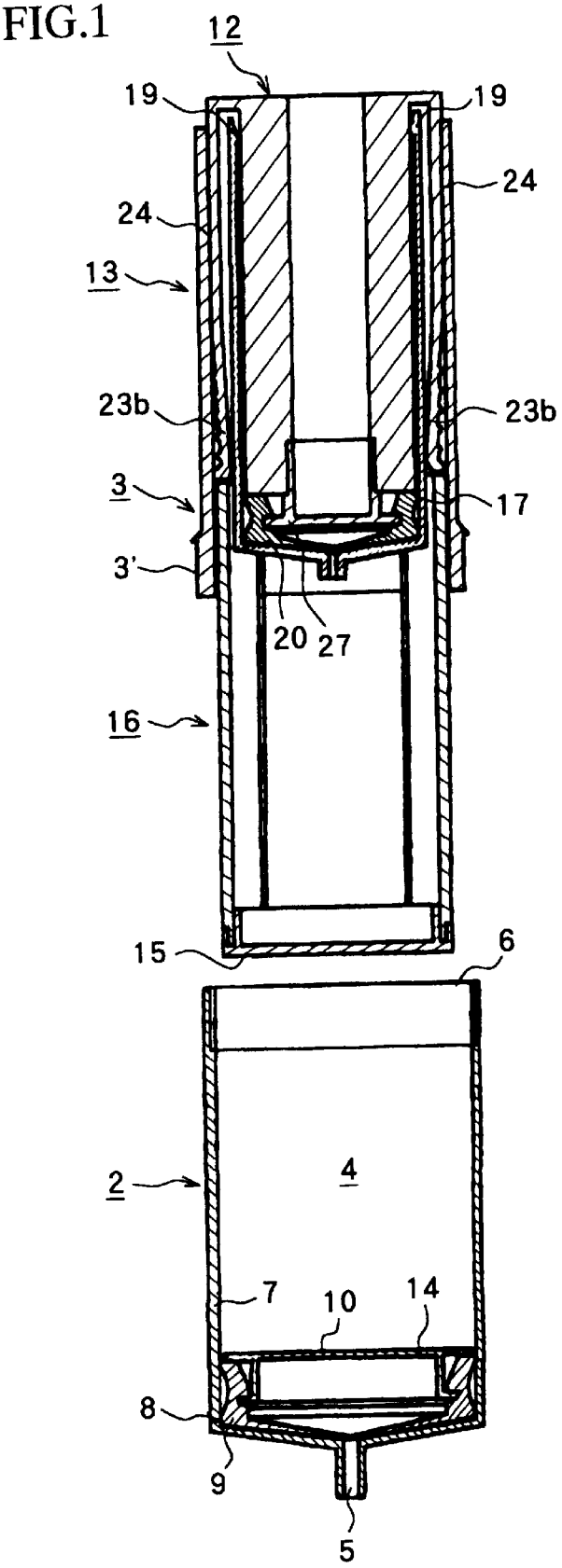
FIG. 1 is a schematic sectional view showing an example of an infusion device of the present invention.

As shown in FIG. 1, the liquid syringe section 2 is provided which has a liquid filling chamber 4 in which liquid is filled and, at one end (a bottom end in the drawing) of the chamber 4, a liquid infusion port 5 through which liquid passes when the liquid is infused, sucked, or the like. The liquid infusion port 5 has a protruding shape so that a liquid tube (not shown) or the like is mounted on a tip thereof in liquid infusion. Further, at the other end (an upper end in the drawing) of the liquid filling chamber 4, an opening 6 to be connected with a bottom end part 3' of the driving pump section 3 is provided.

Inside the liquid filling chamber 4, provided is a pushing member 9 having a peripheral edge 8 which is in sliding contact with an inner peripheral wall 7 of the chamber 4. The pushing member 9 is inserted and fitted into the liquid filling chamber 4 so that it can slide and reciprocate in an axis direction air-tightly and liquid-tightly. On an outer surface (an opening 6 of the liquid syringe section 2) of the pushing member 9, a pressure receiving member 10 is provided.

The liquid syringe section 2 is formed of transparent or semi-transparent material so that liquid filled therein can be confirmed from the exterior, and it may have a tick mark for confirming an amount of the filled liquid on an outer peripheral surface thereof.

The driving pump section 3 has a liquid pushout plunger barrel 12 and a vacuum pump barrel 13 as shown in FIG. 1.

Figure 5A:
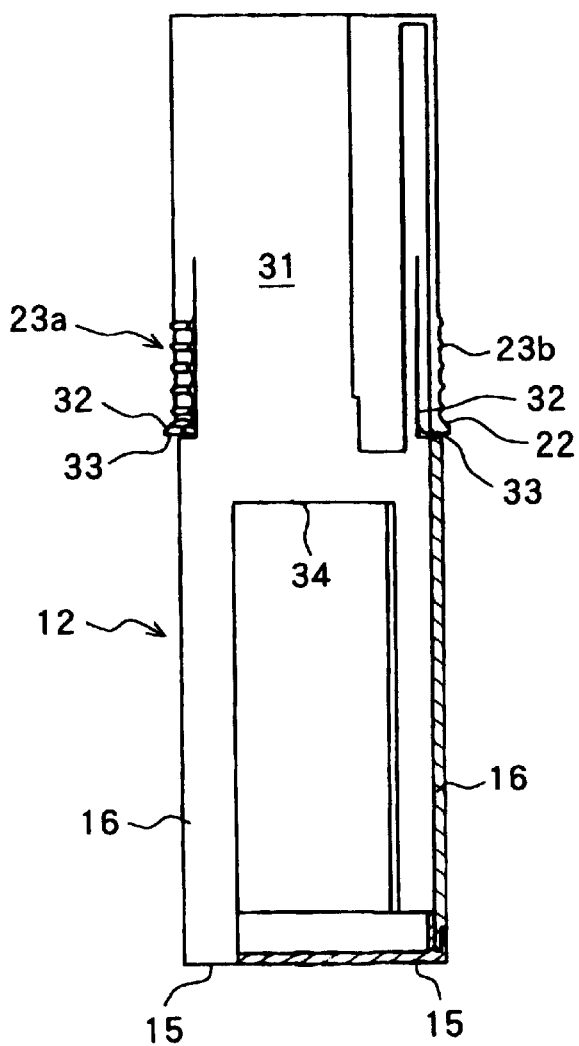
FIG. 5(A) is a partially-cutaway plan view.
Figure 5B:
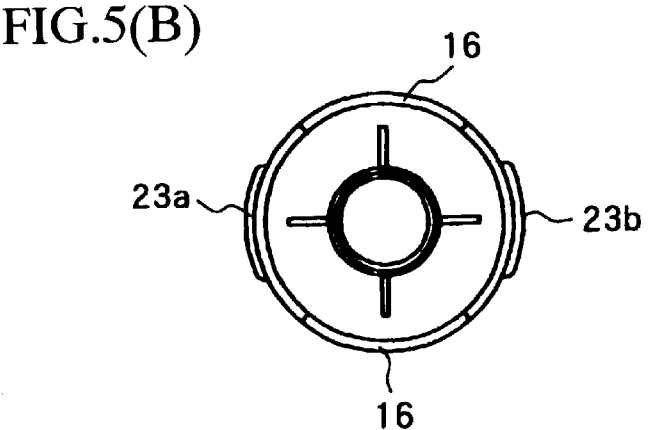
FIG. 5(B) is a bottom view explaining the structure of a liquid pushout plunger barrel of the infusion device of the present invention.

As shown in FIGS. 5(A) and 5(B), the liquid pushout plunger barrel 12 has a base part 31 in a substantially cylindrical shape, from which two pressing arms 16 having a bottom end part 15 which abuts on an upper edge 14 of the pushing member 9 of the liquid filling chamber 4 extend, and two locking stoppers 23a and 23b are formed on an outer periphery of the base part 31. The locking stoppers 23a and 23b has a tongue-shape due to substantially U-shaped grooves 32 which are formed on the outer periphery of the base part 31, and have locking hooks 22 on their tongue end side. The locking stoppers 23a and 23b are structured as elastic members due to the grooves 32 and when force is given from upper parts of the locking hooks 22, the locking stoppers 23a and 23b are inwardly deformed and operated to release engagement with members which abut on their tips 33.

Figure 6A:
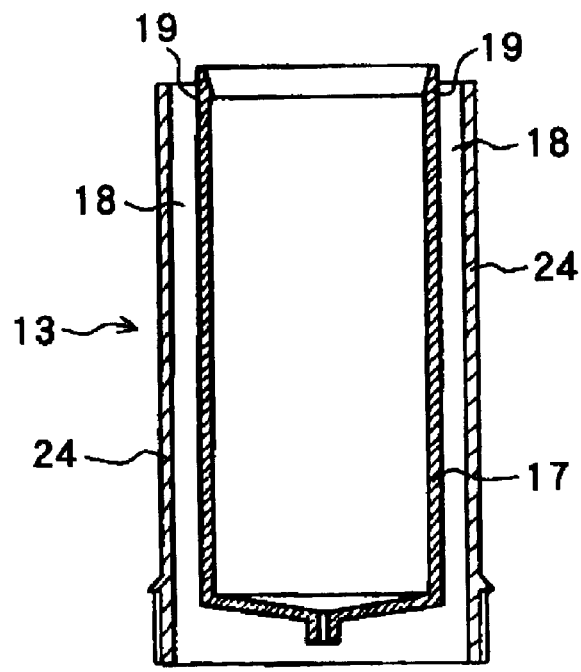
FIG. 6(A) is a horizontal sectional view.
Figure 6B:
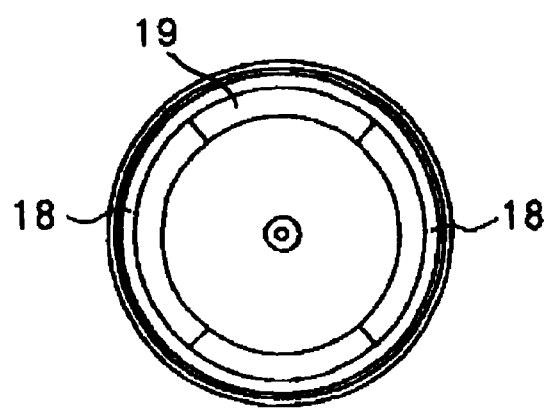
FIG. 6(B) is a bottom view explaining the structure of a vacuum pump barrel of the infusion device of the present invention.

The vacuum pump barrel 13 has, as shown in FIGS. 6(A) and 6(B), circumferential groove parts 18 in a cylindrical shape through which the two pressing arms 16 of the liquid pushout plunger barrel 12 pass, and is structured of an internal negative pressure cylinder 17 which is slidably concentrically inserted into the liquid filling chamber 4 between the circumferential groove part 18 along the inner circumferential wall, and of an outer barrel part 24 externally provided on the pressing arms 16 of the liquid pushout plunger barrel 12. At a tip of the internal negative pressure cylinder 17, tip sliding parts 19 are formed in sliding contact with inner walls of circumferential groove parts 18 which is provided inside the liquid pushout plunger barrel 12.

Furthermore, in the internal negative pressure cylinder 17, a piston member 20, which is in sliding contact with an inner wall thereof air-tightly, is inserted and fitted as shown in FIG. 1. The piston member 20 is connected to a piston holding member 27 mounted on an inner bottom end 34 of the base part 31 of the liquid pushout plunger barrel 12.

In the aforementioned infusion device 1 of the present invention, the pushing member 9 is first inserted from an opening 6 to a liquid infusion port 5 side and arranged in the liquid filling chamber 4 of the liquid syringe section 2, and the pressure receiving member 10 is inserted and fitted into the pushing member 9. Next, the driving pump section 3 is assembled. The assembly is performed in a manner that the piston member 20 is inserted and fitted into the piston holding member 27 which has been mounted on the inner bottom end 34 of the base part 31 of the liquid pushout plunger barrel 12 and the two pressing arms 16 are inserted into the circumferential groove parts 18 of the vacuum pump barrel 13. At this time, inner surface tips of the tip sliding parts 19 of the internal negative pressure cylinder 17 are in sliding contact with inner surfaces of the circumferential groove parts 18 of the liquid pushout plunger barrel 12.

Figure 2:
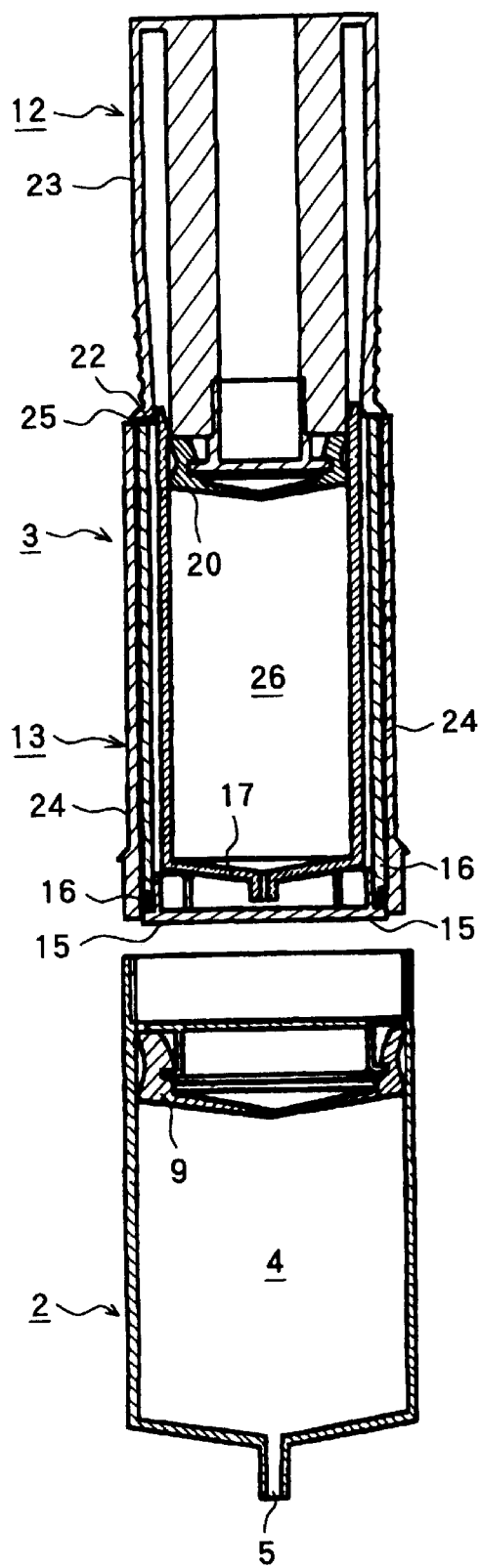
FIG. 2 is a schematic sectional view explaining preparation for operation of the infusion device of the present invention.

Subsequently, as shown in FIG. 2, liquid is infused from the liquid infusion port 5 of the liquid syringe section 2 to push up the pushing member 9 in its axis direction so that the liquid filling chamber 4 is filled with liquid.

Meanwhile, in the driving pump section 3, for example, after placing the driving pump section 3 into an upright position with the liquid pushout plunger barrel 12 placed upward, the outer barrel part 24 of the vacuum pump barrel 13 is pushed down toward the bottom end part 15 of the pressing arms 16 to push down the internal negative pressure cylinder 17 in an axis direction of the driving pump section 3. Consequently, a negative pressure chamber 26 is formed in the internal negative pressure cylinder 17. At this time, the piston member 20 is locked and fixed since the locking hooks 22 at tips of a periphery part of the liquid pushout plunger barrel 12 are directed outward and abut on end parts 25 of the outer barrel part 24. The piston member 20 slides in the internal negative pressure cylinder 17 and maintains a state in which the negative pressure chamber is formed in the internal negative pressure cylinder 17. It is very effective that the negative pressure chamber 26 can be sufficiently created in the driving pump section 3 with such small force as to push down the outer barrel part 24.

Figure 3:
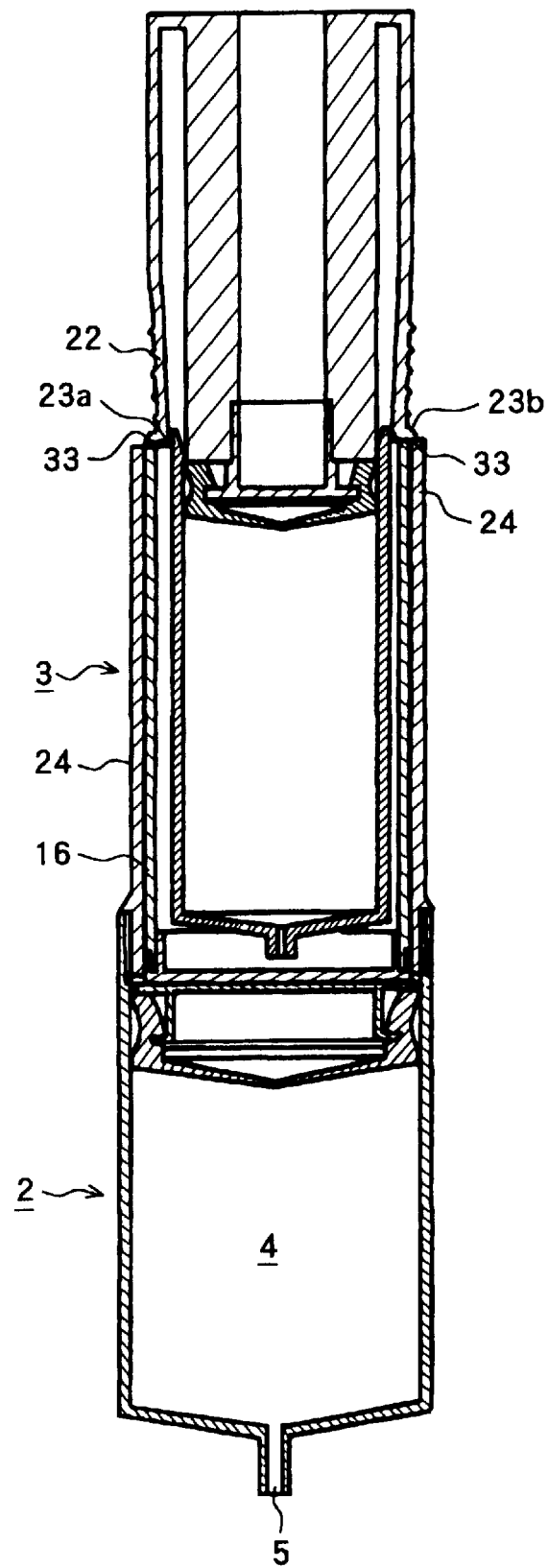
FIG. 3 is a schematic sectional view explaining an assembling state of the infusion device of the present invention.
Figure 4:
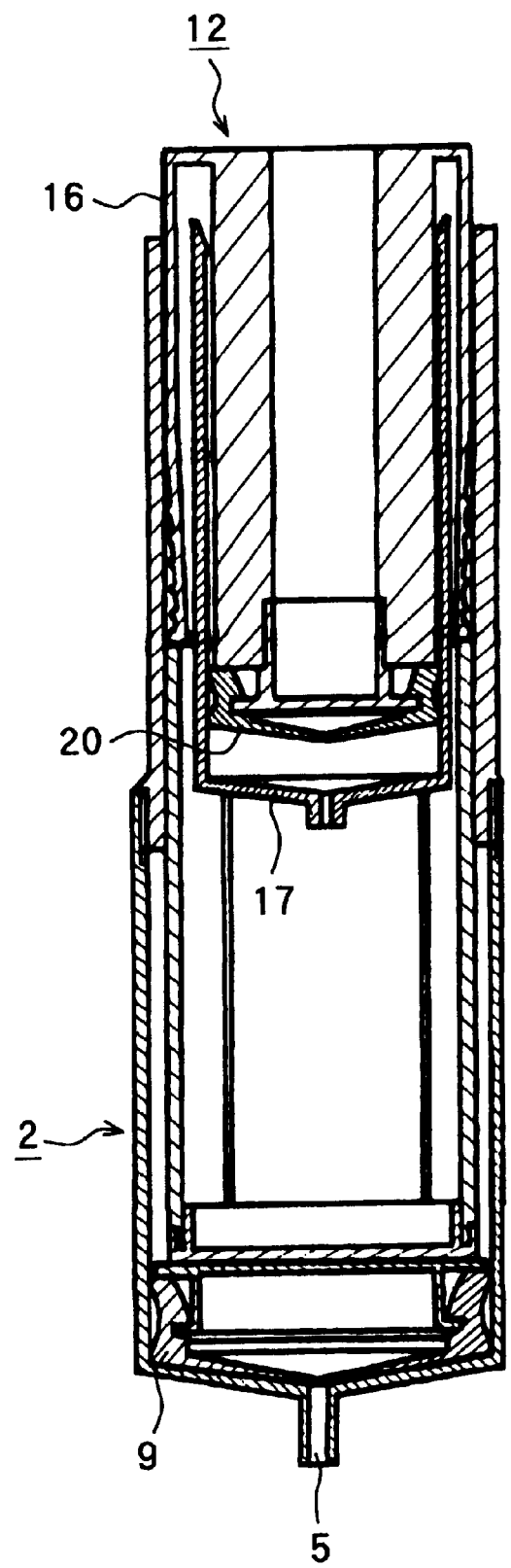
FIG. 4 is a schematic sectional view explaining discharge operation of liquid by the infusion device of the present invention.

Then, as shown in FIG. 3, operational preparation for infusion of the infusion device 1 of the present invention is completed when pressing arms 16 of the driving pump section 3 is connected to the opening 6 of the liquid syringe section 2 in which the liquid filling chamber 4 is filled with liquid. Thereafter, when receiving force from the upper parts of the locking hooks 22, the two locking stoppers 23a and 23b formed on the outer periphery of the base part 31 of the liquid pushout plunger barrel 12, are inwardly deformed to release the engagement with the outer barrel part 24 which abuts on the tips 33. Then, while the tips of the two locking stoppers 23a and 23b are inserted into the circumferential groove parts 18 between the internal negative pressure cylinder 17 and the outer barrel part 24, the pressing arms 16 of the liquid pushout plunger barrel 12 connected to the piston member 20 are biased toward the upper edge of the pushing member 9 due to returning force of the piston member 20 to a bottom end of the internal negative pressure cylinder 17 in the negative chamber 26 to eliminate negative pressure produced in the negative pressure chamber 26 as shown in FIG. 4. And the biased pushing member 9 pushes liquid in the liquid syringe section 2 out of the liquid infusion port 5 to infuse the liquid.

Thus, since the infusion device 1 of the present invention is of the separation type in which the liquid syringe section 2 and the driving pump section 3 are separately structured, less members are to be disposed of and remaining members can be used repeatedly, which is effective in reducing pollution caused by wastes.

Figure 7A:
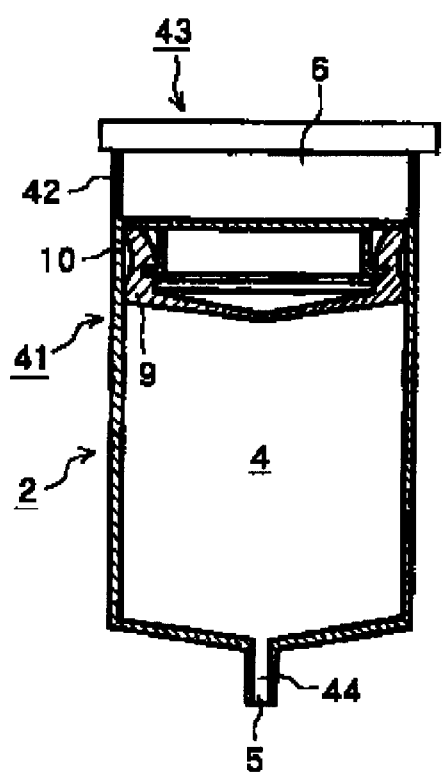
FIG. 7(A) is a schematic sectional view of a liquid cartridge used for a liquid syringe section of the infusion device of the present invention and FIG. 7(B) is a schematic sectional view of the liquid cartridge in an assembly state.
Figure 7B:
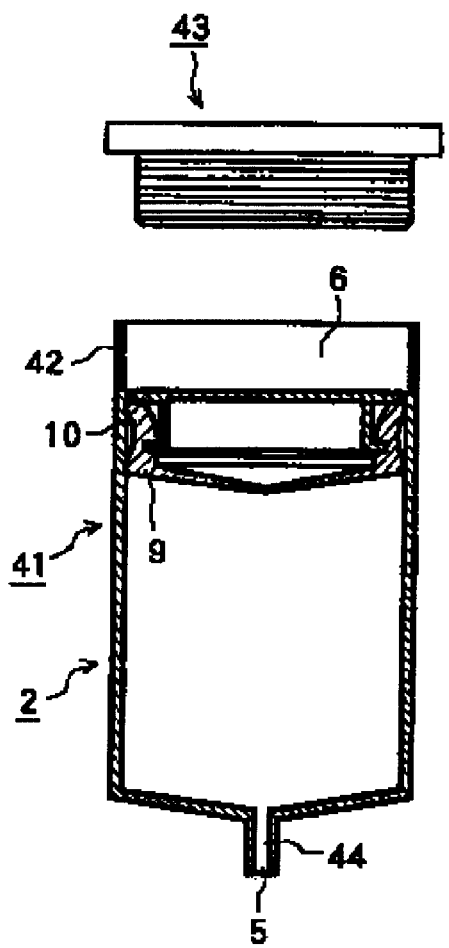

Moreover, in the separation type infusion device 1 of the present invention, the liquid syringe section 2 may take a form of a liquid cartridge 41 which can be filled with liquid and sealed in advance as shown in FIGS. 7(A) and 7(B). The liquid cartridge 41 of this form is removable in which a liquid filling chamber 4 is filled with liquid in advance and a cover 43 is screwed with a screw part 42 formed inside an opening 6. Further, a liquid infusion port 5 is blocked with an elastic blocking member 44 made of rubber or the like or a cap (not shown) capable of sealing the liquid infusion port 5, and a pushing member 9 and a pressure receiving member 10 inserted and fitted into the pushing member 9 are mounted in the liquid filling chamber 4.

Needless to say, in a case where liquid is infused by using the liquid cartridge 41 of the above-described form, liquid infusion can be performed by mounting a driving pump section in which a negative pressure chamber is formed, similarly to the aforementioned case shown in the FIG. 1 to FIG. 6, after the cover 43 is removed from the opening 6 of the liquid syringe section 2. Further, in the case where the liquid cartridge of this form is used, the liquid cartridge can be made available for use in a form that it is filled with liquid and sealed in advance, which has an advantage of ensuring labor-saving and security in filling.

Figure 8A:
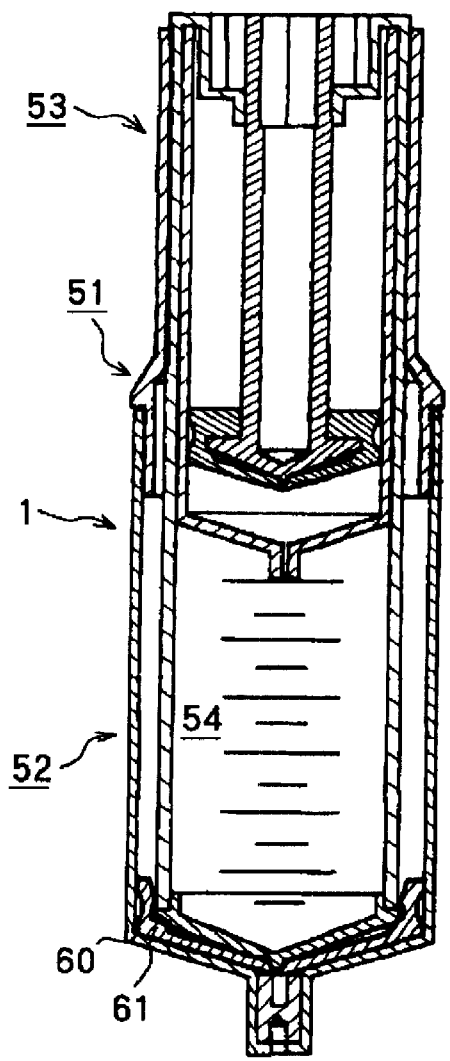
FIGS. 8(A) and (B) are schematic sectional views showing another example of the infusion device of the present invention.
Figure 8B:
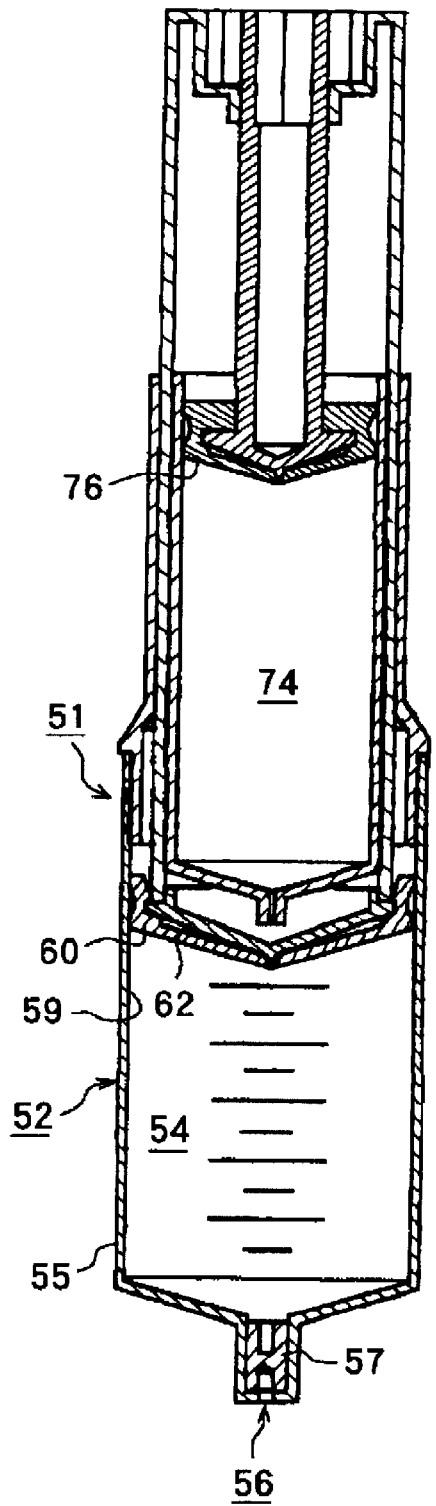
Figure 9:
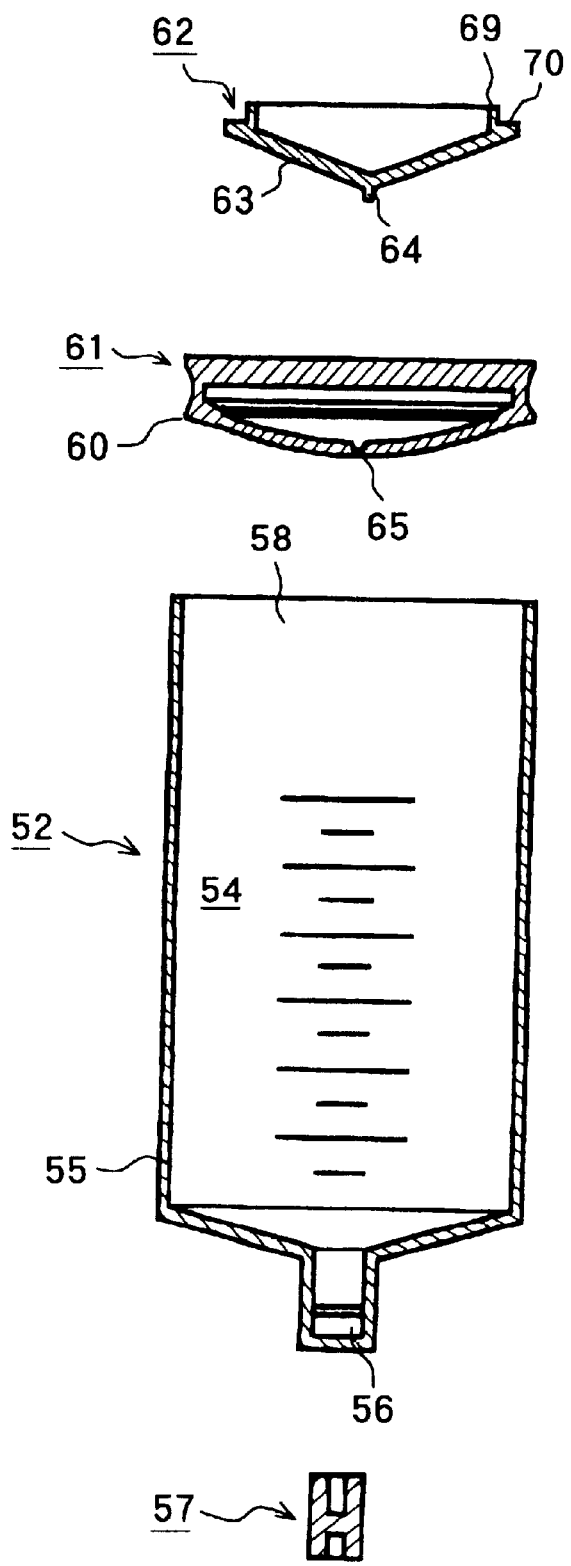
FIG. 9 is a schematic sectional view explaining the structure of a liquid syringe section of the infusion device in FIG. 8.

FIG. 8 to FIG. 13 show another example (infusion device 51) of the infusion device 1 of the present invention. FIGS. 8(A) and 8(B) are diagrams for explaining the whole structure and an operational mechanism of the infusion device 51. The infusion device 51 has a liquid syringe section 52 and a driving pump section 53. The liquid syringe section 52 has a liquid syringe 55 including a liquid filling chamber 54 which is filled with liquid and, at one end of the liquid syringe 55 provided is a liquid infusion port 56 through which liquid passes during liquid infusion or suction or the like into the liquid filling chamber 54, as shown in FIG. 9.

An elastic blocking member 57 is inserted and fitted into the liquid infusion port 56. The elastic blocking member 57 has a function of holding an injection needle or the like connected with a liquid tube or the like when the injection needle is inserted from the exterior and, if the injection needle is held in such a manner, liquid flows out also through the injection needle by the operation of the driving pump section 53. In this case, it is necessary that the elastic blocking member 57 is locked against liquid pressure. Needless to say, the cap is luer-locked for use.

At another end of the liquid syringe 55, an opening 58 connected with a bottom end part of the driving pump section 53 is provided. Further, in the liquid filling chamber 54, a pushing member 61 having a peripheral edge 60 which is in sliding contact with an inner circumferential wall 59 of the liquid filling chamber 54 is internally provided. The pushing member 61 can slidingly reciprocate in an axis direction of the liquid filling chamber 54 air-tightly and liquid-tightly due to the peripheral edge 60. Moreover, a pressure receiving member 62 is inserted and fitted into the pushing member 61. A convex 64 protrudingly provided on a cone-shaped crest part 63 of the pressure receiving member 62 is inserted and fitted into a concave 65 provided inside a crest part of the pushing member 61.

The liquid syringe 55 is formed of transparent or semi-transparent material so that liquid filled therein can be confirmed, and may have a tick mark for confirming an amount of liquid filled in the liquid filling chamber 54 on an outer peripheral surface of the liquid syringe 55.

Figure 11A:
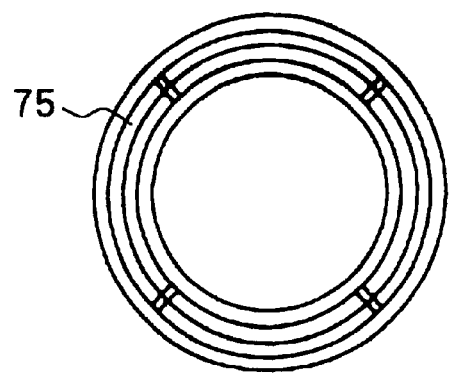
FIG. 11(A) is a top view.
Figure 11B:
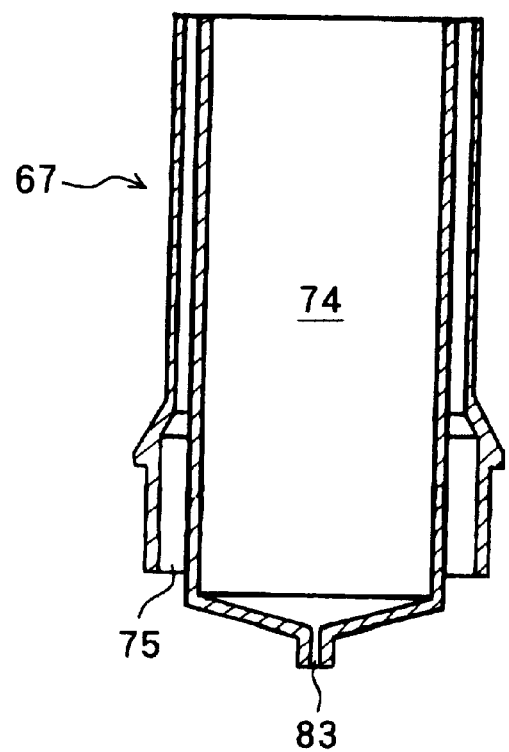
FIG. 11(B) is a horizontal sectional view explaining the structure of the liquid pushout plunger barrel of the driving pump section of the infusion device in FIG. 8.
Figure 12:
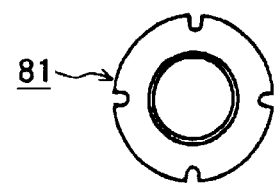
FIG. 12 is an explanatory view of components of an internal negative pressure cylinder of the driving pump section of the infusion device in FIG. 8.
Figure 12:
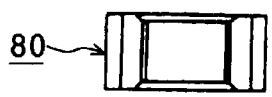
Figure 12:
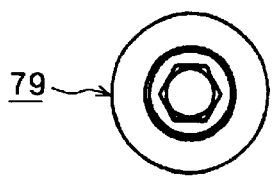
Figure 12:
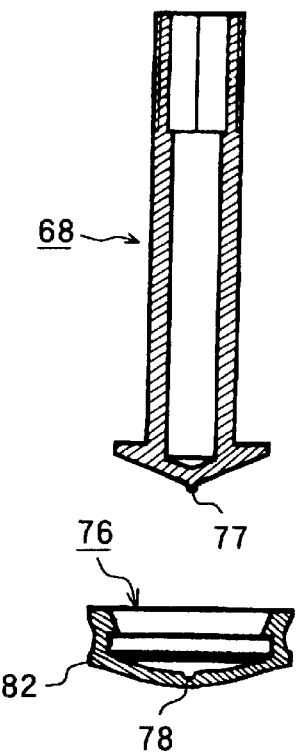

The driving pump section 53 is structured of members shown in FIG. 10 to FIG. 12. Specifically, it is structured of a liquid pushout plunger barrel 66, an internal negative pressure cylinder 67, and an internal negative pressure cylinder member 68.

Figure 10A:
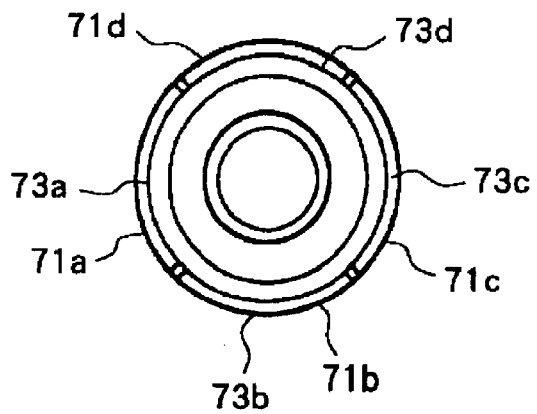
FIG. 10(A) is a bottom view.
Figure 10B:
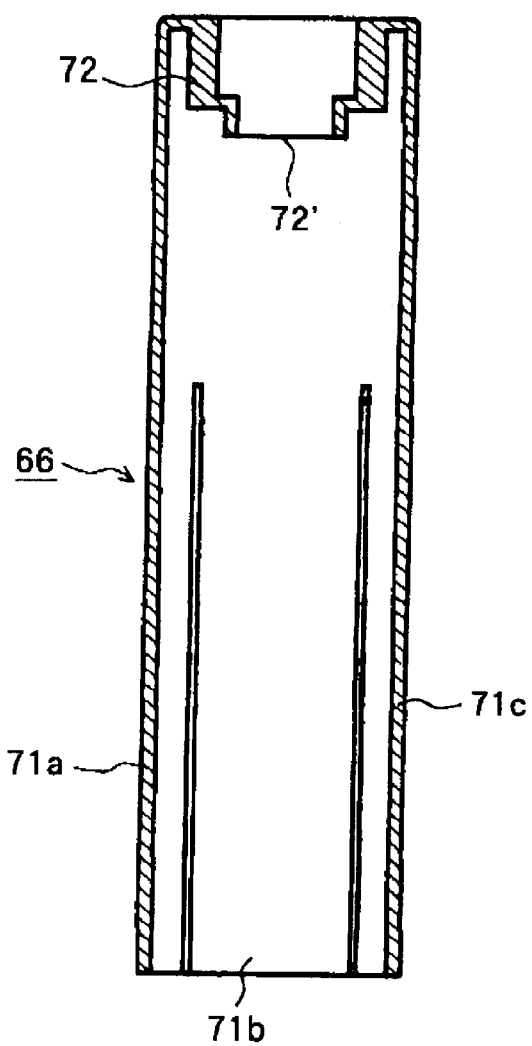
FIG. 10(B) is a horizontal sectional view.
Figure 10C:
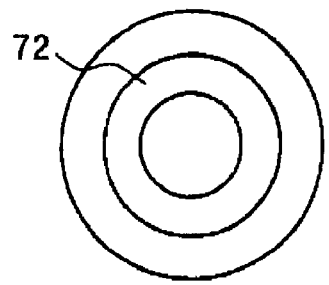
FIG. 10(C) is a top view explaining the structure of a liquid pushout plunger barrel of a driving pump section of the infusion device in FIG. 8.

The liquid pushout plunger barrel 66 has, as shown in FIGS. 10(A) to 10(C), outer peripheral arms 71a, 71b, 71c, and 71d, which are divided substantially arcuate-shaped cross sections, abutting on a receiving part 70 provided in an upper peripheral edge 69 of the pressure receiving member 62 which is inserted and fitted into the pushing member 61, and an upper cover 72 having an opening 72' in its center at an upper end side of the outer peripheral arms 71a, 71b, 71c, and 71d. The outer peripheral arms 71a, 71b, 71c, and 71d are slidably inserted into the liquid filling chamber 54 through arcuate-shaped insertion ports 75 which are bored in lower parts of internal negative pressure cylinder 67 along the inner circumferential wall of the liquid filling chamber 54 so that end parts 73a, 73b, 73c, and 73d abut on the receiving part 70.

The internal negative pressure cylinder 67 has a negative pressure chamber 74 therein as shown in FIG. 11(B), and the insertion ports 75 through which the outer peripheral arms 71a, 71b, 71c, and 71d of the liquid pushout plunger barrel 66 pass are formed around it as shown in FIG. 11(A). In the negative pressure chamber 74, a piston member 76 inserted and fitted into an end part of the internal negative pressure cylinder member 68 shown in FIG. 12 slides in an axis direction air-tightly so as to produce negative pressure.

At a bottom of the piston member 76, a concave 78 is provided. A convex 77 protrudingly provided at a bottom end of the internal negative pressure cylinder member 68 is to be inserted and fitted to the concave 78. At an upper end of the internal negative pressure cylinder member 68, a clamping member 79, a fixing member 80, and a screwing member 81 are screwed and fitted in the described order so that the internal negative pressure cylinder member 68 is clamped and fixed on the upper cover 72 of the liquid pushout plunger barrel 66.

Further, the piston member 76 can be made of elastic material such as rubber so that its side edge part 82 is in close contact with an inner wall of the negative pressure chamber 74 and functions to maintain the inside of the negative pressure chamber 74 to be air-tight.

Figure 13A:
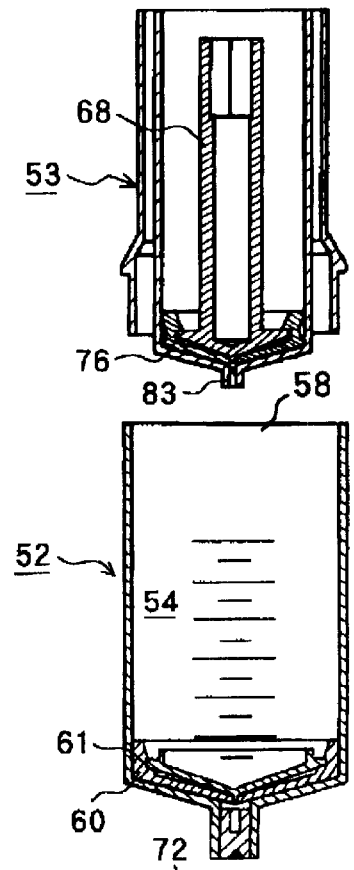
FIGS. 13(A) to 13(D) are explanatory views of an assembling order of the infusion device in FIG. 8.

In the infusion device 51 of this example, the pushing member 61 (and the pressure receiving member 62) is first inserted into the liquid filling chamber 54 of the liquid syringe section 52 to be arranged at an inner bottom thereof as shown in FIG. 13(A). Meanwhile, in the driving pump section 53, the internal negative pressure cylinder member 68 with the piston member 76 mounted at its tip is inserted into the negative pressure chamber 74 to its deep end and a bottom port 83 of the internal negative pressure cylinder 67 is blocked with an inner stopper.

Figure 13B:
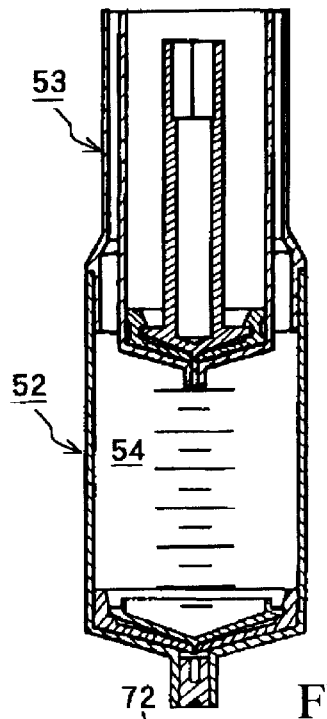
Figure 13C:
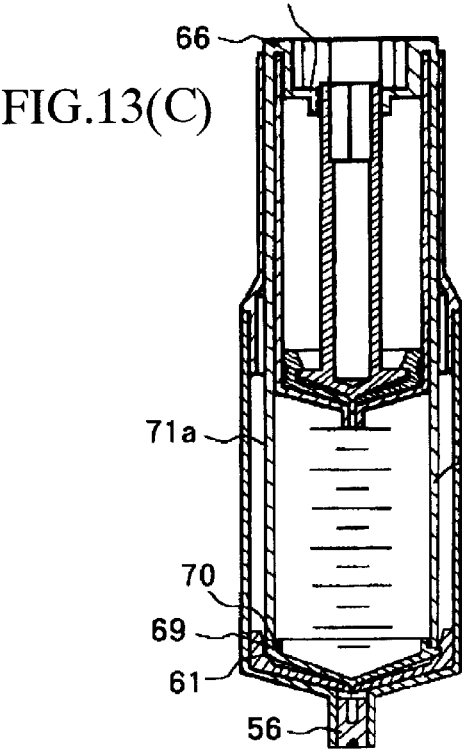
Figure 13D:
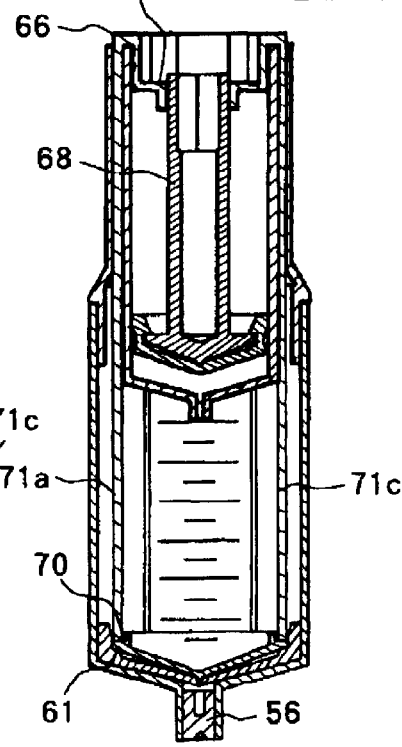

Then, as shown in FIG. 13(B), the driving pump section 53 is connected to the liquid syringe section 52 by mounting it to the opening 58 of the liquid syringe section 52 and, as shown in FIG. 13(C), the outer peripheral arms 71a, 71b, 71c, and 71d of the liquid pushout plunger barrel 66 are inserted into the liquid filling chamber 54 through the arcuate-shaped insertion ports 75 so that each of their end parts abuts on the receiving part 70 provided in the upper peripheral edge 69 of the pressure receiving member 62. Further, the clamping member 79, the fixing member 80, and the screwing member 81 are screwed and fitted from an upper end side of the liquid pushout plunger barrel 66 so that the internal negative pressure cylinder member 68 is clamped and fixed on the upper cover 72 of the liquid pushout plunger barrel 66, as shown in FIG. 13(D). As a result, a spare vacuum is produced in the internal negative pressure cylinder.

The infusion device 51 thus assembled first introduces liquid from a device for filling liquid into the liquid filling chamber 54 by inserting an injection needle or the like into the liquid infusion port 56 of the liquid syringe 55, in an assembly state shown in FIG. 8(A). Since infusion pressure occurring at this liquid introduction pushes the pushing member 61 of the liquid pushout plunger barrel 66 in an axis direction of the liquid syringe section 52, the outer peripheral arms 71a, 71b, 71c, and 71d are pushed up in the axis direction and the piston member 76 arranged inside the outer peripheral arms 71a, 71b, 71c, and 71d slides air-tightly in the axis direction in the negative pressure chamber 74 so that negative pressure is produced. On this occasion, blocking the device for filling liquid inserted into the liquid infusion port 56 or the liquid tube or the like communicated therewith results in maintaining negative pressure inside the negative pressure chamber until liquid infusion starts, and thus preparation for liquid infusion operation is completed as shown in FIG. 8(B).

Next, by opening the liquid tube or the like communicated with the liquid infusion port 56 and utilizing returning force of the piston member 76 due to the negative pressure inside the negative pressure chamber 74, the pushing member 61 is biased to the inner bottom of the liquid syringe section 52, and liquid inside the liquid filling chamber 54 is pushed out of the liquid infusion port 56 to infuse liquid.

The infusion device of this example is advantageous in that the structure of the whole device can be compact and the liquid filling and infusing operation is simplified.

Figure 14A:
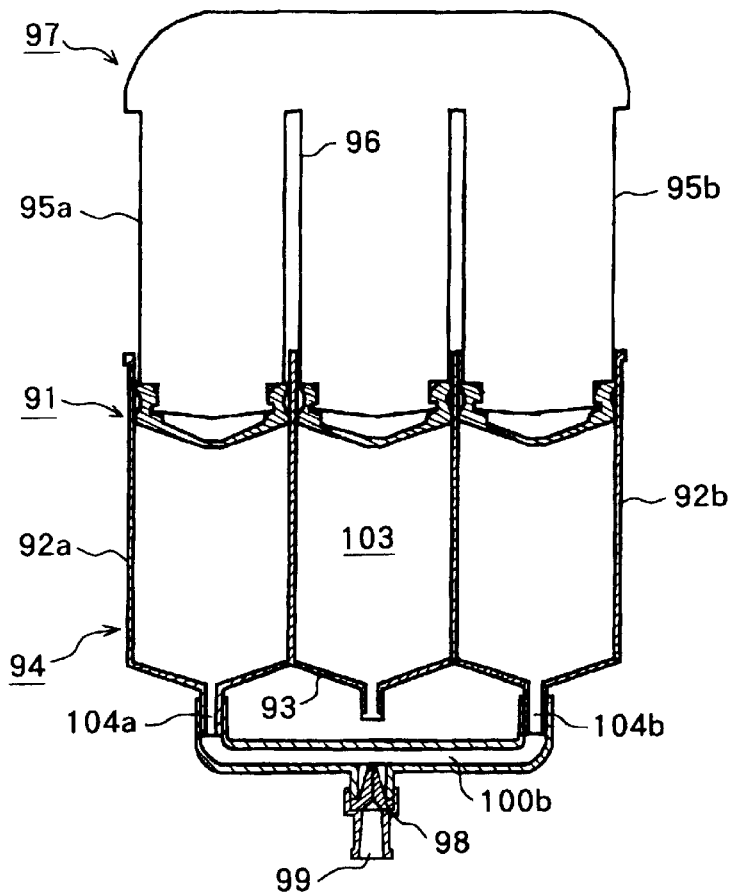
FIGS. 14(A) and 14(B) are schematic sectional views showing still another example of the infusion device of the present invention.
Figure 14B:
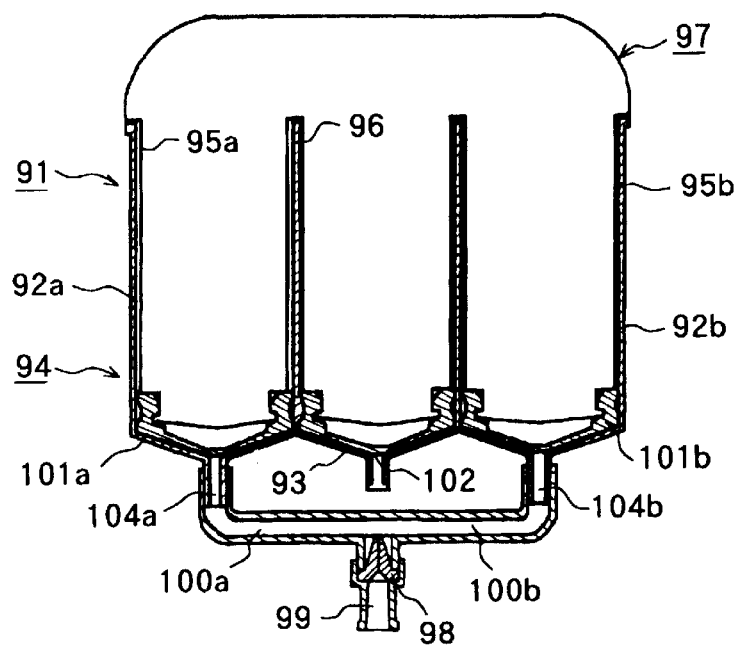
Figure 15:
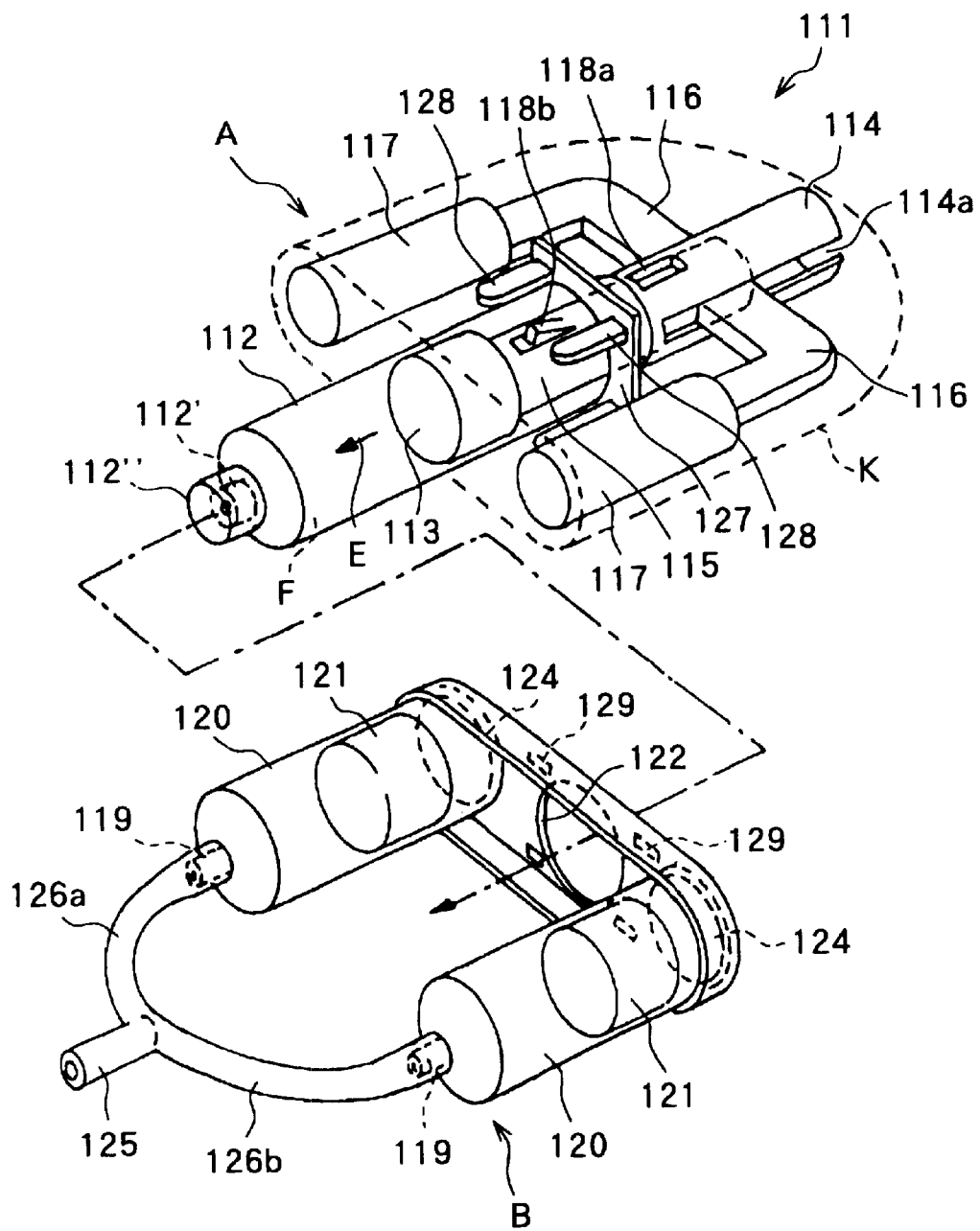
FIG. 15 is a perspective view showing yet another example of the infusion device of the present invention.

FIG. 14 shows still another example (infusion device 91) of the infusion device 1 of the present invention. The infusion device 91 shown in FIGS. 14(A) and 14(B) has a triple type liquid syringe section 94 including two auxiliary syringe parts 92a and 92b provided outside and a central part vacuum pump barrel 93. Further, it has a triple type plunger 97 in which liquid pushout plunger barrels 95a and 95b respectively inserted and fitted into the two auxiliary syringe parts 92a and 92b of the liquid syringe section 94 and a plunger 96 inserted and fitted into the vacuum pump barrel 93 are connected in parallel. Furthermore, the two auxiliary syringe parts 92a and 92b are communicated with each other via communication paths 100a and 100b branching from a liquid infusion port 99 provided with a check valve 98 inside.

Moreover, in the triple type plunger 97, at tips of the liquid pushout plunger barrels 95a and 95b, pushing members 101a and 101b are mounted respectively and structured to slide in the auxiliary syringe parts 92a and 92b liquid-tightly. Further, at a tip of the plunger 96, a piston member 102 is mounted and structured to slide in the vacuum pump barrel 93 air-tightly. These pushing members 101a and 101b and the piston member 102 can be the same as the pushing member and the piston member respectively in the infusion device shown in FIG. 1 to FIG. 13.

In the infusion device 91 shown in FIG. 14, when the triple type plunger 97 is mounted on the liquid syringe section 94, the liquid pushout plunger barrels 95a and 95b are inserted and fitted into the auxiliary syringe parts 92a and 92b as well as the plunger 96 into the vacuum pump barrel 93. Next, liquid is infused to fill the auxiliary syringe parts 92a and 92b from the liquid infusion port 99 through the check valve 98 and the communication paths 100a and 10b, and the pushing members 101a and 101b are biased to push and retract the liquid pushout plunger barrels 95a and 95b. At this time, the plunger 96 connected with the liquid pushout plunger barrels 95a and 95b is also retracted together with the piston member 102 so that a negative pressure chamber 103 is formed in the vacuum pump barrel 93. When liquid infusion stops, the negative chamber is maintained, and operational preparation of the infusion device is completed. Subsequently, when a liquid tube or the like is connected to the liquid infusion port 99 of the liquid infusion device 91 to open the check valve, the liquid pushout plunger barrels 95a and 95b are biased to slide toward liquid outlets 104a and 104b by returning force of the plunger 96 due to negative pressure in the negative chamber 103, the pushing members 101a and 101b push out and discharge liquid, that is, discharge from the liquid infusion port 99 through the communication paths 100a and 100b.

The infusion device 91 of this example may have a compact form, which prevents upsizing, particularly, an increase in thickness of the device, and is effective in terms of convenience to a user of the infusion device to infuse liquid while moving or carrying it.

FIG. 15 to FIG. 20 show yet another example (infusion device 111) of the infusion device 1 of the present invention. The infusion device 111 is composed of a first structure A and a second structure B. The first structure A includes a vacuum pump barrel 112 with an open/close valve 112" put on a ventilation pipe 112' provided at a front end thereof, and a piston 113 air-tightly fitted into the vacuum pump barrel 112. The piston 113 is formed integrally with a front end of an inner barrel 115 which is fitted into a cylindrically-shaped outer barrel 114 coaxially connected from a rear end of the vacuum pump barrel 112 so that the inner barrel 115 can slide in an axis direction. Incidentally, a rear half part of the first structure A may be covered with a cover member K as shown by a broken line in FIG. 15.

In side middle parts of the outer barrel 114, long grooves 114a and 114a are formed in bilaterally symmetrical positions. A horizontal member 116 orthogonally fitted and fixed into a horizontal groove 115a, which is provided at a rear end of the inner barrel 115, is put through the bilateral long grooves 114a and 114a. At both ends of the horizontal member 116, cylindrically-shaped (or possibly column-shaped) pushers 117 and 117 movable in a direction coaxial with the piston 114 are integrally provided extending in a forward direction.

Between the outer barrel 114 and the inner barrel 115, a stopper 118 is provided. When pulled backward (a pushers side is pushed backward while fixing a rear end of the outer barrel 114, refer to FIG. 18), the piston 113 in the vacuum pump barrel 112 is given force in a pushing back direction (direction shown by an arrow E) due to atmospheric pressure under the influence of a negative pressure area F which is formed at the front end of the vacuum pump barrel 112, but the stopper 118 is provided to maintaining the pulled-back state of the piston 113 against the force (atmospheric pressure).

Figure 16:
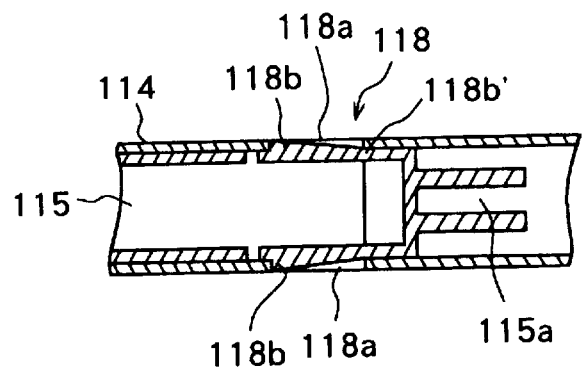
FIG. 16 is a sectional view showing the structure of a stopper for locking a piston of a vacuum pump barrel against atmospheric pressure.

The stopper 118 can have any structure but is structured as shown in FIG. 16 in this example. Specifically, the stopper 118 is composed of rectangular through holes 118a and 118a provided along an axis direction on upper and lower surfaces of the cylindrically-shaped outer barrel 114, which is connected to the rear end of the vacuum pump barrel 112, and wedge-shaped pieces 118b and 118b integrally provided on upper and lower surfaces of the inner barrel 115, which has the piston 113 at its front end.

The wedge-shaped pieces 118b has steps formed at the side of a piston 113, and the steps protrude from hinge parts 118b' due to elasticity of material. The wedge-shaped pieces 118b move in sliding contact with upper and lower inner surfaces of the outer barrel 114 in a normal state. However, when the piston 113 is pulled to reach the through holes 118a and 118a, the wedge-shaped pieces 118b are fitted into and locked with the through holes 118a and 118a. Accordingly, when the engagement is released by pushing the locked upper and lower wedge-shaped parts 118b and 118b with fingers through the through holes 118a and 118a, the piston 113 is pushed back by atmospheric pressure.

Further, the second structure B includes liquid syringes 120 having liquid ports 119 at their front end and pistons 121 liquid-tightly fitted into the liquid syringes 120. According to this example, the dual liquid syringes 120 are fixed on both ends of a frame 123 having a through hole 122 at its center, through which the vacuum pump barrel 112 of the first structure A is put (triple or more liquid syringes 120 are provided in some cases in accordance with a shape of the frame 123). In fixed parts of the frame 123 on which the dual liquid syringes 120 are fixed, through holes 124 and 124 through which the pushers 117 and 117 can pass respectively are formed. It is recommended to temporarily bond hermetic seals (not shown) on the holes 124 and 124. Furthermore, each of the liquid ports 119 of the dual liquid syringes 120 is communicated to one conduit 125 via bifurcated pipes 126a and 126b. At a tip of the conduit 125, an injection needle or the like is mounted via a not-shown flow rate adjusting device and connected to a liquid-transfusion place such as the vessel of a patient.

The first structure A is provided with a flange 127 whose front face abuts on a rear face of the frame 123 of the second structure B when the vacuum pump barrel 112 passes through the through hole 122 from the rear of the frame 123. From a front face side of the flange 127 and around the vacuum pump barrel 112, square pieces (pins) 128 extend. The square pieces 128 can be fitted into through holes 129 provided around the through hole 122 of the frame 123.

Incidentally, although not shown in the drawing, the square pieces 128 and the through holes 129 facing the square pieces 128 may be provided oppositely. Specifically, the through holes may be provided in the flange 127 while the square pieces may be provided around the through hole 122 of the frame 123 toward the rear.

Figure 17:
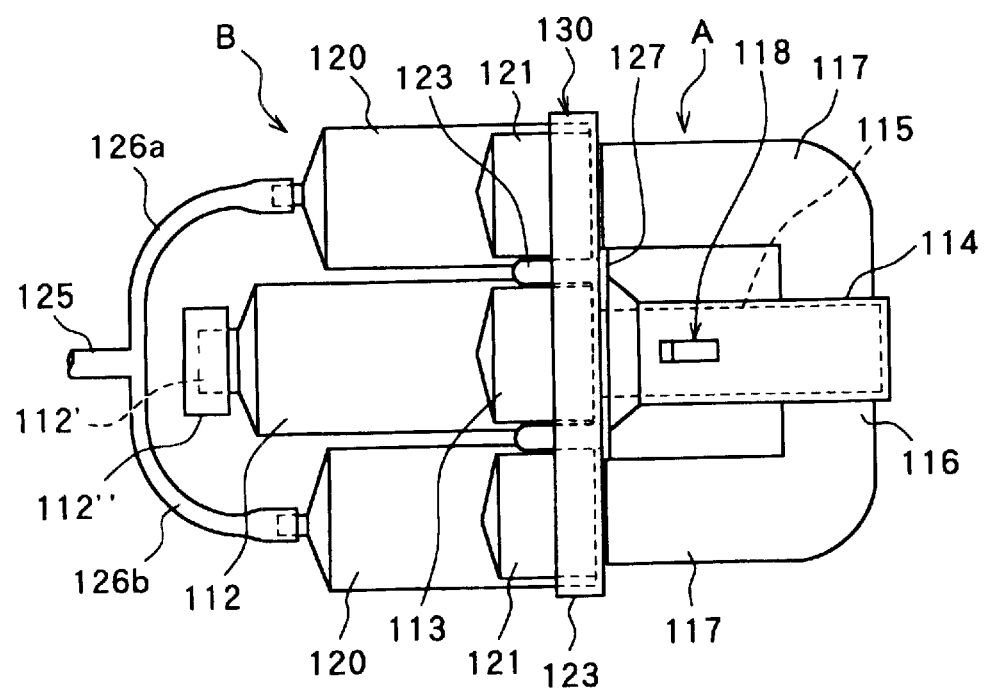
FIG. 17 is a plan view of the infusion device in FIG. 15.

The flange 127, the square pieces 128 around the flange 127, the through hole 122 of the frame 123, and the through holes 129 around the through hole 122 compose a connector 130 between the first structure A and the second structure B. In other words, the first structure A and the second structure B can be removably connected as shown in FIG. 17 in a state that the pistons 121, which have moved to the rear end because a predetermined amount of liquid is infused into the liquid syringes 120, are arranged in front of the pushers 117 which have been locked with the stopper 118 against atmospheric pressure by pulling the piston 113 of the vacuum pump barrel 112.

The first structure A when connected with the second structure B functions as a driving mechanism for continuously pushing, with the pushers 117, the pistons 121 in the liquid syringes 120 of the second structure B through the through holes 124 and 124 by utilizing returning force of the piston 113 of the vacuum pump barrel 112 by the atmospheric pressure.

When the second structure B is disconnected with the first structure A, liquid infusion into the liquid syringes 120 is performed relatively lightly through the conduit 125 because it is performed only against sliding resistance of the pistons 121 without making a negative pressure area.

Incidentally, liquid is infused into the liquid syringes 120 each time when necessary according to a purpose such as treatment at a medical site, or performed in advance in a pharmaceutical plant. In the latter case, it is recommended to temporarily bond the hermetic seals (not shown) on the through holes 124 and 124 of the frame 123 on which the liquid syringes 120 are fixed so that the pistons 121 are not brought into direct contact with air including dust and the like during transportation.

Next, the operation of the above-described infusion device 111 will be explained. First, the open/close valve 122" of the ventilation pipe 112' provided at the front end of the vacuum pump barrel 112 of the first structure A is closed. Then, the negative pressure area F is formed in the vacuum pump barrel 112.

Figure 18:
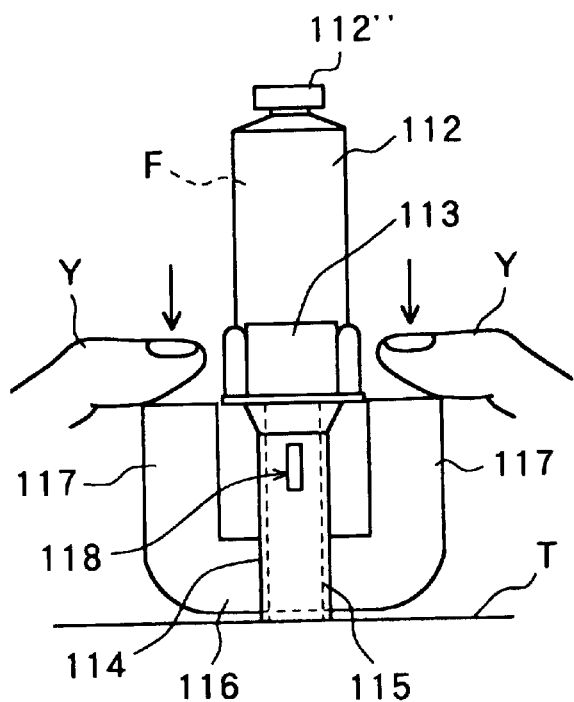
FIG. 18 is a view showing how a negative pressure area is formed in a vacuum pump barrel of a first structure.
Figure 19:
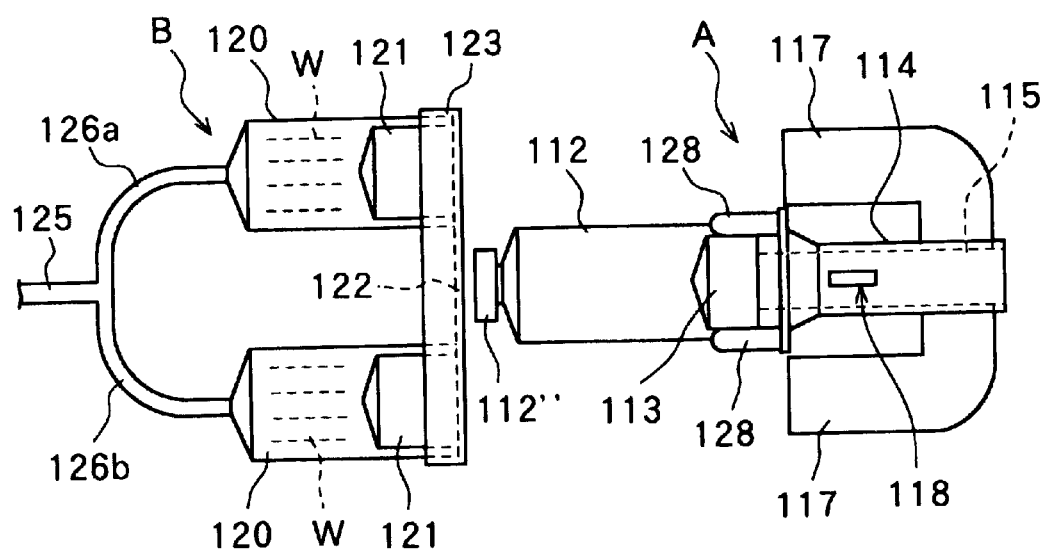
FIG. 19 is an explanatory view of the infusion device of the present invention immediately before the first structure and a second structure are connected.

As an example of attaining the formation shown in FIG. 18, an user fixes the rear end of the outer barrel 114 of the first structure A on a desk top face T or the like in a an erect position, and pushes the pushers 117 and 117 with his thumbs Y to a direction indicated by arrows while lightly holding a base body with his both hands (with his palms in case the user does not have enough power). This pushes down the piston 113 in the vacuum pump barrel 112 against atmospheric pressure, thereby forming the negative pressure area F at the front end of the vacuum pump barrel 112.

In the present invention as described above, the formed negative pressure area can be performed completely separately from liquid infusion into the liquid syringes. The formation of the negative pressure area can be maintained by locking the stopper 118 provided between the outer barrel 114 and the inner barrel 115.

Subsequently, liquid is infused into the liquid syringes 120 of the second structure B through the conduit 125 by using an injector (not shown) or the like. The liquid infusion is performed relatively lightly against the sliding resistance of the pistons 121 which are in sliding contact with the liquid syringes 120 liquid-tightly. Liquid W has pushed the pistons 121 to the rear end of the liquid syringes 120 when liquid infusion into the liquid syringes 120 is complete (refer to FIG. 19).

Figure 20A:
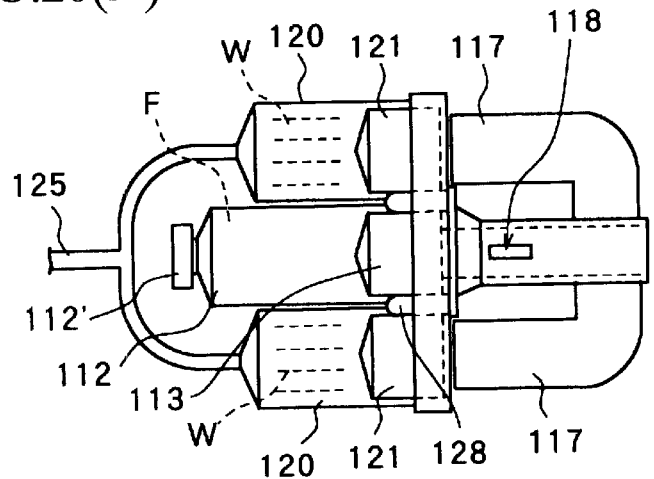
Figure 20B:
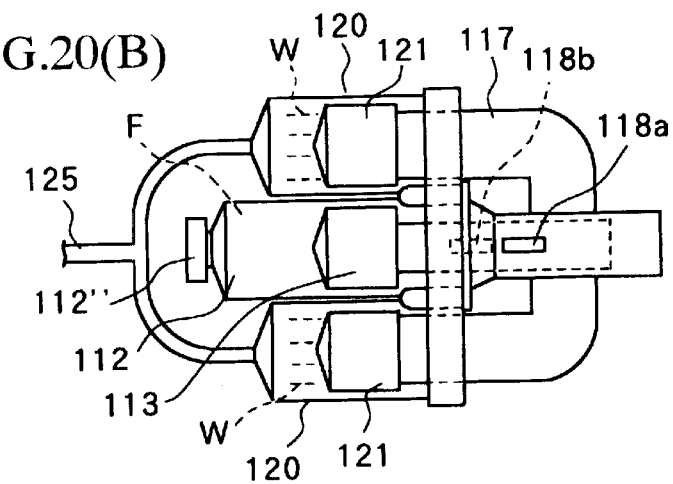

Thereafter, the front end of the vacuum pump barrel 112 of the first structure A is made to face the through hole 122 of the frame 123 of the second structure B (refer to FIG. 19) from the rear thereof, and then the vacuum pump barrel 112 is put into the through hole 122 to engage the square pieces 128 on the front face of the flange 127 with the insertion holes 129 of the frame 123. As a result, the first structure A and the second structure B are connected with each other so that the pistons 121, which is positioned at the rear end of the liquid syringes 120 of the second structure B having infuse liquid, faces to the pushers 117 of the first structure A as shown in FIG. 20(A) (a standby state). At this time, the piston 113 in the vacuum pump barrel 112 of the first structure A is in the locked state by the stopper 118 against the atmospheric pressure, as described above.

Next, the tip of the conduit 125 is connected to the liquid-transfusion part such as the vessel of a patient by the injection needle which is mounted via the flow rate adjusting device, and then the wedge-shaped pieces 118b of the stopper 118 of the first structure A are pushed with fingers through the through holes 118a to release the engagement. As a result, the piston 113 is pushed back by atmospheric pressure so that the pistons 121 of the liquid syringes 120 are pushed via the pushers 117 for a little while to continuously infuse liquid (venous injection) into a body (refer to FIG. 20(B)).

Figure 20C:
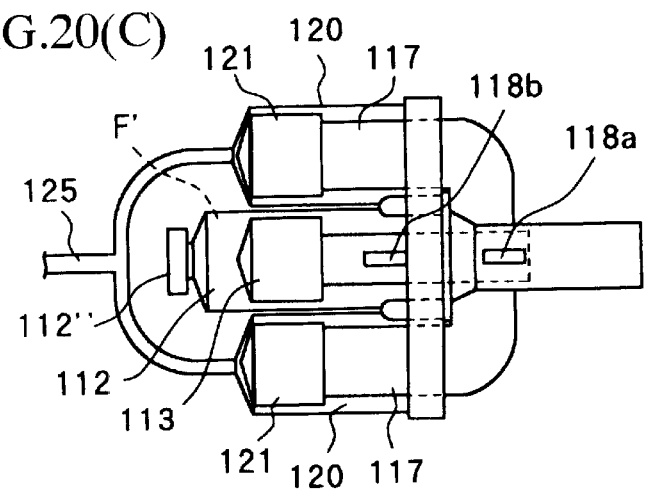

Thus, infusion (venous injection) of liquid is complete as shown in FIG. 20(C). In the above-described connection state, the front end of the vacuum pump barrel 112 of the first structure A extends further forward than the front ends of the liquid syringes 120 and therefore a spare vacuum part F' is formed in a vacuum pump barrel 112 side so that driving force thereof does not change (decrease) until liquid in the liquid syringes 120 is completely infused into the body.

After the aforementioned venous injection is completed, the tip of the conduit 125 is disconnected from the liquid-transfusion part and the second structure B is separated from the first structure A and disposed. At the time of separating the second structure B, if the four square pieces 128 of the first structure A are pushed with the fingers of both hands to a direction of the insertion holes 129, the action of the spare vacuum part F' helps the second structure B be easily separated from the first structure A.

Thereafter, to prepare for the next use, the open/close valve 112" of the ventilation pipe 112' provided at the front end of the negative syringe 112 of the first structure A is turned to an open side. In other words, the second structure B of a liquid syringe side is disposable while the first structure A of a vacuum pump barrel side is repeatedly used.

As described above, the present invention achieves liquid infused into the liquid syringe with smaller force compared with that required for a conventional liquid infusion device which utilizes negative pressure. In addition, the small driving pump section thereof further enables operational preparation with small force, and facilitates intra-arterial infusion requiring pressure of 300 mmHg or more. The liquid infusion device of the present invention is easy to handle because of its simple structure, and it has separable liquid syringe section and driving pump section and also has cost advantage. Further, it is capable of infusing liquid at constant infusion rate and amount of liquid with not too large leakage of air and sliding resistance. It is excellent in durability. Further, when the liquid syringe section and the driving pump section are separated, only the liquid syringe section is disposable and the driving pump section is reusable for multiple times, which is advantageous in terms of cost and effective in reducing pollution caused by wastes.

The invention is not limited to the above embodiments and various modifications may be made without departing from the spirit and scope of the invention. Any improvement may be made in part or all of the components.

What is claimed is:

1. A continuous liquid infusion device comprising:
   a liquid syringe section; and
   a driving pump section to be mounted on said liquid syringe section, wherein:
   said liquid syringe section has a liquid infusion port at one end and an opening at the other end connected with a bottom end part of said driving pump section; a liquid filling chamber in communication with the liquid infusion port; and a pushing member including a peripheral edge in sliding contact with an inner circumferential wall of the liquid filling chamber, the pushing member being slidable due to the peripheral edge to reciprocate liquid-tightly and air-tightly in an axis direction of said liquid syringe section;
   said driving pump section has a liquid pushout plunger barrel and an internal negative pressure cylinder to be inserted and fitted into the liquid pushout plunger barrel, the liquid pushout plunger barrel including the bottom end part abutting on an upper edge of the pushing member and at least two pressing arms in connection with the bottom end part and to be inserted and fitted into the liquid filling chamber along the inner circumferential wall, and the internal negative pressure cylinder containing a negative pressure chamber and having a piston inserted and fitted thereinto, the piston sliding in the axis direction of the negative pressure chamber air-tightly to produce negative pressure; and
   by sliding the pressing arms of said driving pump section toward an upper end, the piston in the negative pressure chamber is slidingly pushed up in the axis direction to produce negative pressure in the negative pressure chamber, and the liquid pushout plunger barrel is biased toward the upper edge of the pushing member via a locking member engaged with the piston by utilizing returning force of the piston due to the negative pressure so that the biased pushing member pushes liquid in the liquid syringe out of the liquid infusion port.

2. The continuous liquid infusion device according to claim 1, wherein
   said liquid syringe section and said driving pump section are separably structured.

3. The continuous liquid infusion device according to claim 1, wherein
   said liquid syringe section is structured of a plurality of auxiliary syringe parts and has pressing arms and bottom end parts corresponding to the pushing members, respectively, the pushing members being inserted and fitted into the plurality of auxiliary syringe parts.

4. The continuous liquid infusion device according to claim 2, wherein
   said liquid syringe section is structured of a plurality of auxiliary syringe parts and has pressing arms and bottom end parts corresponding to the pushing members, respectively, the pushing members being inserted and fitted into the plurality of auxiliary syringe parts.

* * * * *